(12) United States Patent
Hawkins et al.

(10) Patent No.: US 6,740,186 B2
(45) Date of Patent: May 25, 2004

(54) METHOD OF MAKING AN ORTHOPEADIC IMPLANT HAVING A POROUS METAL SURFACE

(75) Inventors: Michael Hawkins, Columbia City, IN (US); Steven James Charlesbois, Goshen, IN (US); Jerry W. Howard, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 304 days.

(21) Appl. No.: 10/079,231

(22) Filed: Feb. 20, 2002

(65) Prior Publication Data

US 2003/0155686 A1 Aug. 21, 2003

(51) Int. Cl.⁷ .............................................. B32B 31/00
(52) U.S. Cl. ........................ 156/242; 156/289; 264/135; 623/901
(58) Field of Search ................................ 156/228, 242, 156/289, 580, 581, 583.1; 264/129, 135; 623/66.1, 901; 128/898

(56) References Cited

U.S. PATENT DOCUMENTS

| | | | | |
|---|---|---|---|---|
| 5,236,457 A | * | 8/1993 | Devanathan | 128/898 |
| 5,504,300 A | * | 4/1996 | Devanathan et al. | 219/121.64 |
| 5,571,187 A | * | 11/1996 | Devanathan | 623/66.1 |
| 5,672,284 A | * | 9/1997 | Devanathan et al. | 219/121.64 |
| 5,773,789 A | * | 6/1998 | Devanathan et al. | 219/121.64 |
| 6,049,054 A | * | 4/2000 | Panchison et al. | 219/121.64 |

* cited by examiner

*Primary Examiner*—James Sells
(74) *Attorney, Agent, or Firm*—Jonathan D. Feuchtwang; Zimmer Technology Inc.

(57) ABSTRACT

An orthopaedic implant having a porous metal surface in a preferred embodiment, the implant comprises three layers including a biocompatible metal core of desired shape, a polymer intermediary layer, and a surface layer comprising a porous biocompatible metal, shaped appropriately to act as the surface of an orthopaedic implant is provided. The core and the pad are placed in an injection molding device wherein a polymer intermediary layer is injection molded between the pad and the metal core, thereby bonding the pad to the metal core.

14 Claims, 2 Drawing Sheets

METHOD OF MAKING AN ORTHOPEADIC IMPLANT HAVING A POROUS METAL SURFACE

RELATED APPLICATIONS

There are no related applications

1. BACKGROUND OF THE INVENTION

The present invention relates generally to orthopaedic implants, and, more specifically, to an orthopaedic implant having a porous biocompatible metal surface layer, or pad.

2. DESCRIPTION OF RELATED ART

It is known to provide an orthopaedic implant covered by a porous layer to promote ingrowth of bone within the openings of the porous layer, thus providing long-term fixation of the implant to the bone. Several methods of accomplishing such bonding are also known.

Diffusion bonding is the most widely known and accepted method of attaching a porous layer to an implant. Diffusion bonding of porous layer to a substrate having a curved surface, such as a portion of a hip stem, however, is not without difficulties. For example, diffusion bonding a porous material to a substrate can cause notches to be formed in the substrate, thereby decreasing the strength of the substrate. Orthopaedic implant manufacturers have successfully compensated for the effect diffusion bonding by either limiting the amount of porous layer attached to the substrate, or by adjusting the size and shape of the substrate to increase its strength.

Nevertheless, diffusion bonding a porous metal pad to an implant body is both time-consuming and expensive from a manufacturing standpoint. For example, the ramp-up and cool down time for a furnace necessary to conduct a diffusion bonding process may be as high as 14 hours per cycle. In some applications, such as diffusion bonding a porous metal pad to the interior bone-engaging surface of a femoral knee component, it may take a minimum of three cycles (42 hours) to complete the diffusion bonding operation.

In order to avoid some of these problems, the Applicant has developed an improved process for bonding a porous metal pad to the surface of an orthopaedic implant comprising diffusion bonding a fiber metal pad to a thin metal foil, then attaching the metal pad to an orthopaedic implant using a laser welding process. (For details of such an attachment process, reference is hereby made to U.S. Pat. No. 5,504,300 entitled "Orthopaedic Implant and Making of Making Same;" U.S. Pat. No. 5,672,284 entitled "Method of Making Orthopaedic Implant by Welding;" U.S. Pat. No. 5,773,789 entitled "Method of Making Orthopaedic Implant Having a Metal Pad;" and U.S. Pat. No. 6,049,054 entitled "Method of Making an Orthopaedic Implant Having a Porous Metal Pad," each of which is assigned to the assignee of the present invention and incorporated herein by reference. In general, each of these patents describes a method for attaching a porous surface to an orthopaedic implant, wherein a porous metal pad, such as a fiber metal pad, is diffusion bonded to a thin metal foil. The fiber metal pad is then configured to be received within a recess formed in an orthopaedic body. The edges of the thin metal foil extend to the exterior of the recess formed in the orthopaedic implant body. A laser welder is used thereafter to weld the thin metal foil to the orthopaedic implant body in various positions, thereby indirectly attaching the fiber metal pad. Laser welding, however, while in some ways, superior to diffusion bonding, or sintering, a porous metal pad directly to an implant body, does require expensive laser welding devices.

Due to the difficulties associated with known means of bonding a porous surface to the core of an orthopaedic implant, attention has been focused on the use of nonmetallic materials for constructing all or a portion of an orthopaedic implant and then bonding the porous metallic surface thereto. Materials such as plastics, composites, ceramics, and thermosets have been used in such devices. Such materials are used in the hope of better matching the flexural rigidity of bone and gaining greater transfer of forces through the implant to the natural bone in order to promote bone growth and stability. U.S. Pat. No. 5,236,457 to Devanathan; and U.S. Pat. No. 5,571,187 also to Devanathan, both assigned to the Applicant, disclose methods of bonding a porous metal and to a polymer layer.

In general, these patents describe a method for producing an orthopaedic implant by providing either a metal core surrounded by a polymer or a completely polymeric implant body; forming a porous surface layer insert; positioning both objects in a mold; and injecting a polymer there between in order to bond the porous surface to the implant body. Thereafter, amorphous polymers that are used to form the porous surface are removed from the implant using a solvent. Although this method produces a successful and safe product, it is desirable to produce a process that does not require extracting amorphous polymer from the porous outer surface, thereby alleviating the necessity of maintaining costly and potentially dangerous solvents at the manufacturing facility. A need exists, therefore, for a method of impregnating an interior surface of a porous metal pad with a polymer film, similar in chemistry to the polymer used in the bonding step. This improvement does not require the use of a solvent to remove amorphous polymer from the outer surface of the impregnated pad. A further need exists for bonding such an impregnated pad with an orthopaedic implant to form an orthopaedic implant having a porous metal surface.

SUMMARY OF THE INVENTION

The invention comprises a method for bonding a porous metal surface to an orthopaedic implant having a plastic body or a substantially solid core surrounded by a plastic body. In addition, the present invention provides a method for impregnating a porous metal pad with a polymer film, such as a polyaryletherketone, to facilitate later bonding of the porous metal surface to a polymer surface.

The method of impregnating a porous metal pad comprises providing a sheet of biocompatible metal, preferably, commercially pure titanium, a sheet of heat-resistant releasable plastic film, generally a polyimide film such as KAPTON™; a sheet of semi-crystalline polymer film, such as polyetheretherkeone, polyaryletherketone or polyphenylenesulfide; a porous metal pad, a second sheet of heat-resistant releasable plastic film and a second sheet of biocompatible metal.

These sheets and the pad are arranged such that the biocompatible metal sheets from the outermost layers and such that the porous metal sheet abuts the semi-crystalline polymer film. The layered arrangement is subsequently positioned into a press for sufficient time and under sufficient conditions to allow the semi-crystalline polymer film to interpose itself within the porous metal, thus producing an impregnated pad.

The method of forming an orthopaedic implant having a porous metal surface comprises providing a porous metal pad of desired size and shape suitable for bonding to an orthopaedic implant, impregnating the porous metal pad, using the method described above, placing the impregnated porous metal pad into a molding device, then molding a polymer into the molding device such that the polymer forms the body of an orthopaedic implant and bonds to at least one surface of the porous metal layer.

In an alternative embodiment, a substantially solid core is placed into the molding device prior to molding a polymer. The core may comprise any biocompatible material including titanium, or a ceramic; however, the core preferably comprises a cobalt chromium molybdenum alloy. When the polymer is molded in the device, it surrounds the core and acts as an intermediary layer between a biocompatible metal core and the porous metal surface of an orthopaedic implant.

In this manner, the present invention provides a method of making an orthopaedic implant having a porous surface without the shortcomings of either laser welding or diffusion bonding. In addition, semicrystaline polymer reduces the processing time require to produce an implant.

These and other advantages of the present invention will be apparent to persons skilled in the art upon reading the present specification and the appended claims.

DETAILED DESCRIPTION OF THE INVENTION

Figure 1:
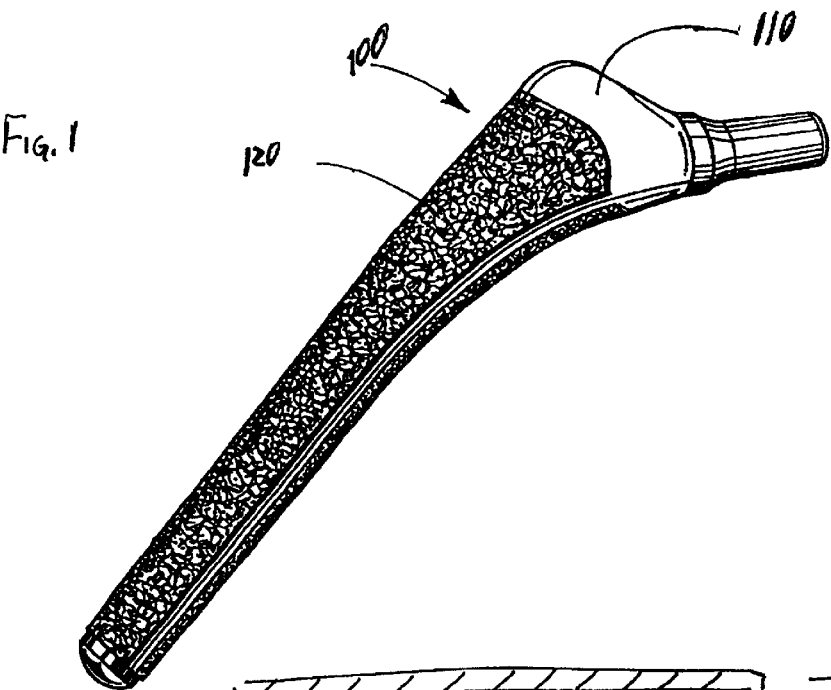
FIG. 1 is a perspective view of an exemplary bone implant according to the present invention.

Referring to FIG. 1, an exemplary prosthetic implant is depicted, although FIG. 1 shows a femoral hip stem, those skilled in the art will understand that the present invention may be applied other endoprosthetic implants, for which it is desirable to have a porous metal surface, for example, the bone contacting surface of a femoral condylar knee implant. The hip stem 1 shown of FIG. 1 includes a body 110 and a porous surface 120. To produce an implant, a porous pad 240 is first formed with a suitable material by any of a variety of known methods. Preferably, it includes biocompatible metal fibers such as titanium and its alloys or cobalt-chromium alloys. Pad 240 may also be produced by sintered metal beads, sintered ceramics or other suitable porous material.

Figure 2:
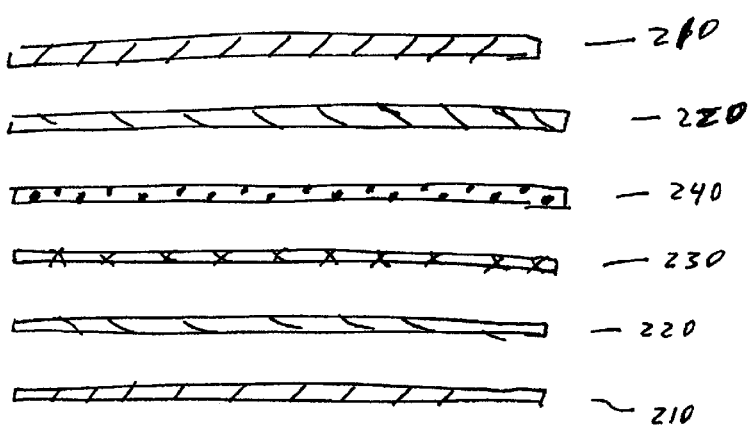
FIG. 2 is an exploded elevational view of the impregnated porous metal pad.
Figure 3:
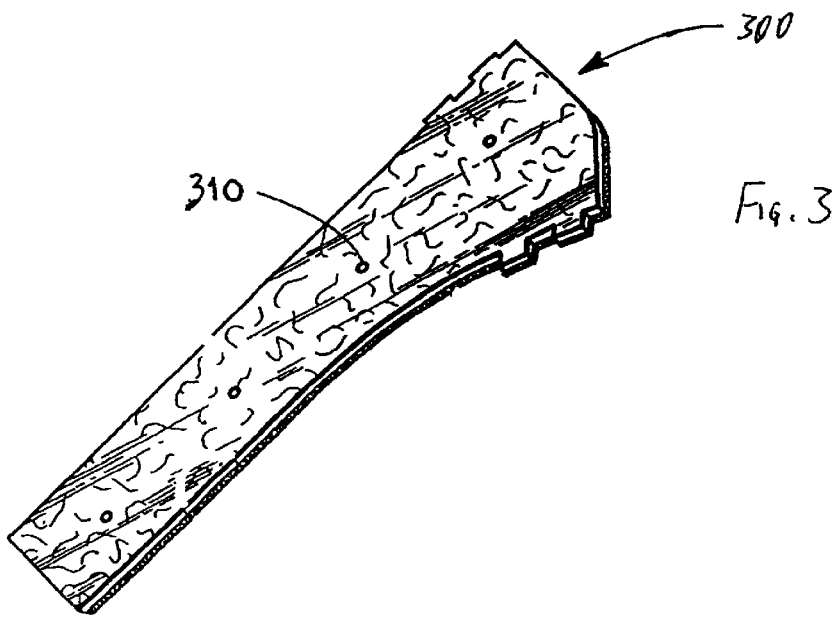
FIG. 3 is a perspective view of an impregnated porous metal pad.

Next, an impregnated porous pad 300, as shown in FIG. 3, is formed. This insert will eventually become the porous surface of an orthopaedic implant according to the present invention. As shown if FIG. 2, the porous surface is formed by impregnating the interior of porous pad 240 with a suitable polymer. This is accomplished by providing a first sheet of biocompatible metal 210, preferably titanium; a first sheet of heat-resistant releasable polyimide film 220; a sheet of semicrystalline polymer film 230; selected from the group consisting of polyetheretherketone, polyacryletherketone and polyphenylenesulfide; porous metal pad 240; a second sheet of heat-resistant releasable plastic film and a second sheet of biocompatible metal 210. These layers are provided such that biocompatible metal sheets 210 form the outermost layers of the arrangement and the pad 240 abuts the semi-crystalline polymer film 230 within the interior of the arrangement. Thereafter, a preferred way of introducing the semi-crystalline polymer film 230 into the pad 240 is to press this layered arrangement together for a sufficient time and under sufficient temperature and pressure to allow the semi-crystalline polymer film 230 to advance into the pad 240 in a controllable manner. Preferably, the pad 240 is cut into a desired shape, impregnated with the semi-crystalline polymer film 230, then formed (if necessary) into its final form. However, porous pad 240 may be impregnated with the semi-crystalline polymer film 230 before being formed into its final shape. In either event, impregnated pad 300 is constructed to include holes 310 that aid in positioning and securing the insert in a mold, such as by pins extending from the mold to engage the holes.

Figure 4:
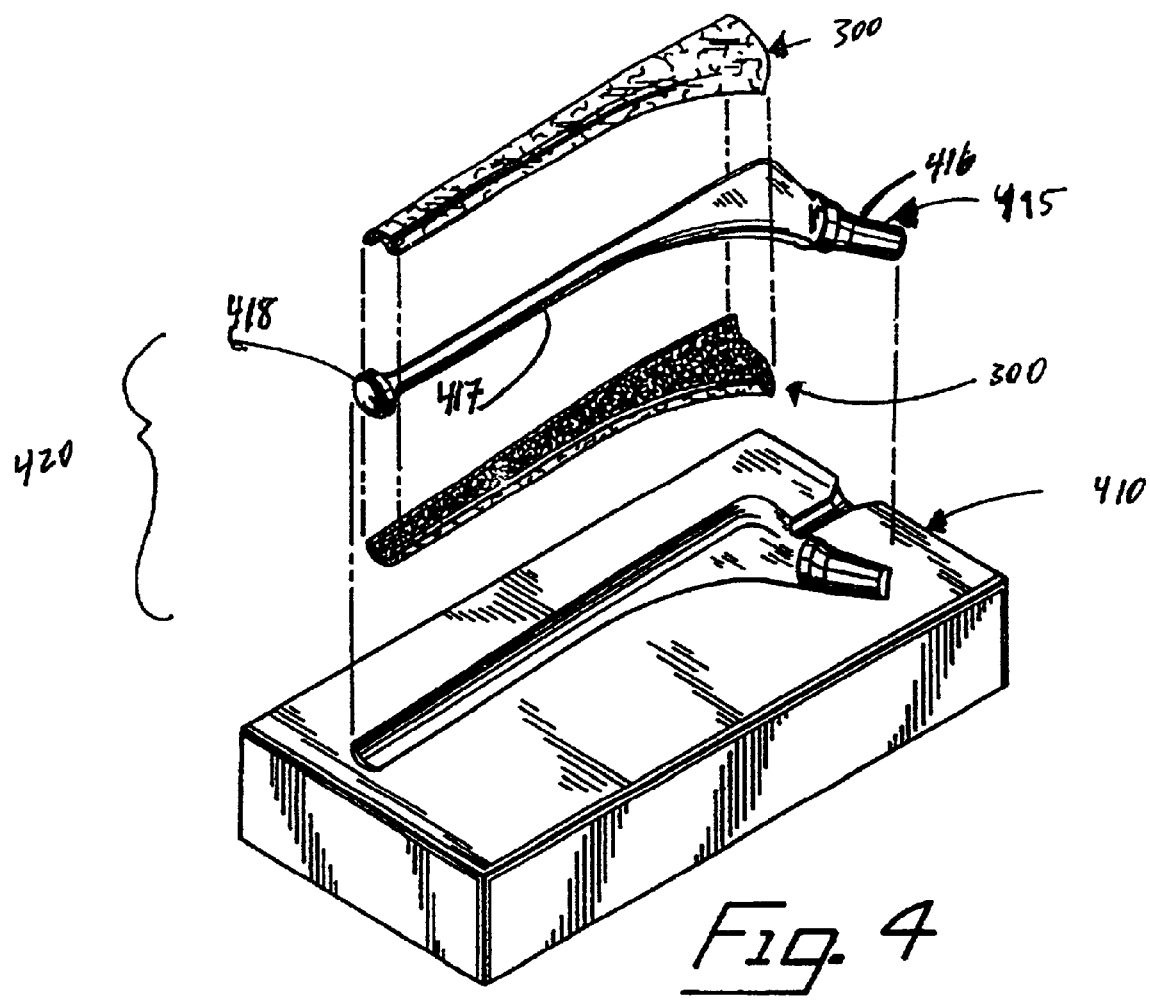
FIG. 4 is an exploded perspective view of an exemplary implant mold and implant.
Figure 5:
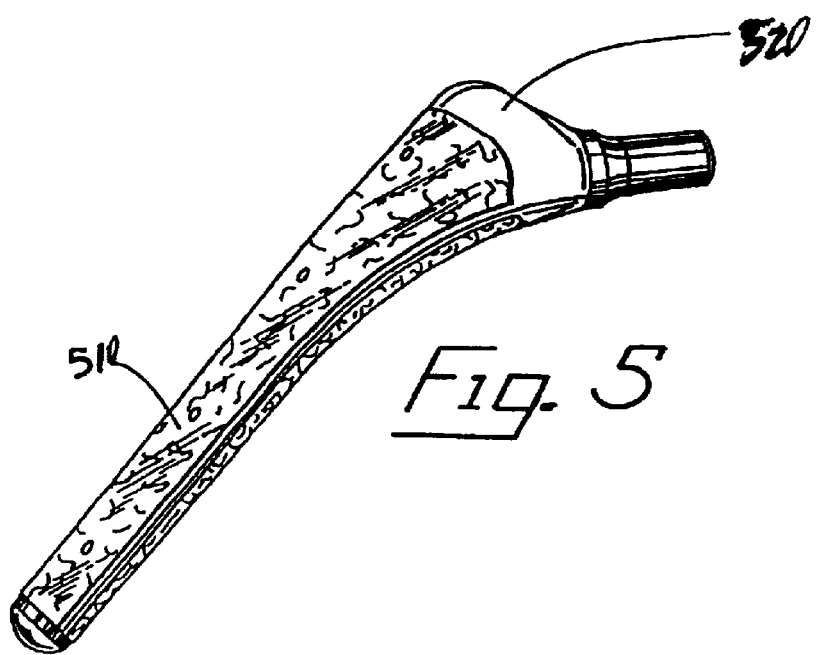
FIG. 5 is a perspective view of an exemplary bone implant according to the present invention having a porous surface, a polymer intermediary layer and a biocompatible metal core (not shown).

At least one impregnated pad 300 is placed in an appropriate mold half 410 with some of the unfilled pores in communication with the mold cavity as shown in FIG. 4. This material will eventually form implant body 420 to which impregnated pad 300 will be bonded. Various molding techniques may be used, including injection molding, compression molding and casting. It is preferable, however, to use injection molding. The impregnated porous pad 300 is constructed such that the impregnation materials prevent the body material from entering the film pores of impregnated pad 300 during molding, but allows it to infiltrate the unprotected pores to establish secure fixation of impregnated pad 300 to the body 420. Preferably, the body material is a semicrystalline polymer such as polyaryletherketone, polyetheretherketone or polyphenylenesulfide. Semi-crystalline polymers such as these are desirable due to their strength, processibility, in general, insolubility in common solvents. If desired, other strengthening agents such as carbon fiber, may be included in the body material.

While the foregoing has described an exemplary and preferred embodiment of the present invention, variations are possible. For example, the materials and methods discussed herein, could be used to produce an implant with a porous surface suitable for any endoprosthetic implant. In addition, other structures could be included in the mold prior to molding the body. Such structures include solid and composite cores, fixation pins, and hollow inserts. In the drawings included herein, a substantially solid core 415 is shown in the mold between two impregnated pads 300. The core 415 is preferably formed of a biocompatible material such as cobalt chromium molybdenum alloy. As shown in FIG. 3, the core 415 has a neck 416, a stem 417, and a button 418. Neck 416 and button 418 engage mold 410 to form seals and prevent the injected material from coating their surfaces.

We claim:

1. A method for impregnating a porous metal pad with a polymer, wherein the method comprises:
   (a) providing a first sheet of biocompatible metal, a first sheet of heat-resistant releasable plastic film, a sheet of semi-crystalline polymer film, a porous metal pad, a second sheet of heat-resistant releasable plastic film, and a second of sheet of biocompatible metal;
   (b) creating an abutting arrangement of the sheets and pad such that the biocompatible metal sheets form the outer most layers of the arrangement, and the porous metal pad abuts the polyaryletherketone film; and
   (c) placing the arrangement into a press for sufficient time and under sufficient temperature and pressure to allow the semi-crystalline polymer film to interpose itself within the porous metal sheet, to form an impregnated porous metal pad.

2. The method of claim 1, wherein the biocompatible metal sheets comprise commercially pure titanium.

3. The method of claim 1, wherein the semi-crystalline polymer film is selected from the group consisting of polyetheretherketone, polyaryletherketone, and polyphenylenesulfide.

4. The method of claim 1, wherein the heat resistant releasable plastic film is a polyimide film.

5. A method of forming an orthopaedic implant having a porous metal surface, the method comprising:

(a) providing a first sheet of biocompatible metal, a first sheet of heat resistant releasable plastic film, a sheet of semi-crystalline polymer film, a porous metal pad, a second sheet of heat resistant releasable plastic film, and a second sheet of biocompatible metal;

(b) arranging the of sheets and the pad, such that the same are each adjacent to at least one other sheet or pad, and that the biocompatible metal sheets form the outermost layers of the arrangement, and the porous metal pad abuts the polyaryletherketone film sheet;

(c) placing the layered arrangement into a press for a sufficient time and under sufficient temperature and pressure to allow the polyaryletherketone film to interpose itself into the porous metal pad, thus forming an impregnated porous metal pad;

(d) placing the impregnated pad into a molding device;

(e) molding a polymer implant body adjacent to the polymer impregnated inner surface or the pad, such that it is bonded to the surface of the implant body.

6. The method of claim 5, wherein the biocompatible metal is titanium.

7. The method of claim 5, wherein the semi-crystalline polymer film is selected from the group consisting of polyetheretherketone, polyaryletherketone and polyphenylenesulfide.

8. The method of claim 5, wherein the heat resistant releasable polymer film is a polyimide film.

9. A method of forming an orthopaedic implant having a core, a polymeric intermediary layer, and a porous metal surface, the method comprising:

(a) providing a substantially solid core;

(b) providing a porous metal pad having a desired size and a desired shape suitable for bonding to the core;

(c) providing a first sheet of biocompatible metal, a first sheet of heat resistant releasable plastic film, a sheet of semi-crystalline polymer film, a second sheet of heat resistant releasable plastic film, and a second sheet of biocompatible metal;

(d) providing an abutting layered arrangement of the sheets and the porous metal pad such that the biocompatible metal sheets form the outermost layer of the arrangement such that the porous metal sheet abuts the polyaryletherketone film sheet;

(e) placing the layered arrangement into a press for sufficient time and under sufficient temperature and pressure to allow the semi-crystalline polymer film to interpose itself into the porous metal pad; thus forming an impregnated porous metal pad;

(f) placing the arrangement and the core into an injection molding device; and (g) injection molding a polymer intermediate layer around the core and between the core and the polymer impregnated inner surface of the pad.

10. The method of claim 9, wherein the metal core comprises a cobalt-chromium-molybdenum alloy.

11. The method of claim 9, wherein the biocompatible metal sheet is commercially pure titanium.

12. The method of claim 9, wherein the heat resistant releasable plastic film is a polyimide film.

13. The method of claim 9, wherein the polymer intermediate layer is selected from the group consisting of polyaryletherketone, polyetheretherketone and polyphenylenesulfide.

14. The method of claim 9, wherein the semi-crystalline polymer is selected from the group consisting of polyaryletherketone, polyetheretherketone and polyphenylenesulfide.

* * * * *